United States Patent [19]

Marosi et al.

[11] 4,404,175

[45] Sep. 13, 1983

[54] PREPARATION OF ZEOLITES

[75] Inventors: Laszlo Marosi, Ludwigshafen; Hans-Ulrich Schlimper, Speyer; Matthias Schwarzmann, Limburgerhof; Joachim Stabenow, Weinheim, all of Fed. Rep. of Germany

[73] Assignee: BASF Aktiengesellschaft, Fed. Rep. of Germany

[21] Appl. No.: 268,379

[22] Filed: May 29, 1981

[30] Foreign Application Priority Data

Jun. 7, 1980 [DE] Fed. Rep. of Germany ....... 3021580

[51] Int. Cl.$^3$ ............................................. C01B 33/28
[52] U.S. Cl. ..................................... 423/329; 423/277; 423/328
[58] Field of Search ................................ 423/326–330, 423/277; 260/448 C; 253/431 N, 455 Z

[56] References Cited

U.S. PATENT DOCUMENTS

| | | | |
|---|---|---|---|
| 3,306,922 | 2/1967 | Barrer et al. | 260/448 C |
| 4,060,590 | 11/1977 | Whittam et al. | 423/329 X |
| 4,139,600 | 2/1979 | Rollmann et al. | 423/329 |
| 4,259,537 | 3/1981 | Chu | 585/475 X |
| 4,299,732 | 11/1981 | Ball et al. | 423/328 X |

FOREIGN PATENT DOCUMENTS

| | | |
|---|---|---|
| 7081 | 1/1980 | European Pat. Off. ............ 423/329 |
| 2442240 | 3/1975 | Fed. Rep. of Germany . |
| 2817575 | 11/1978 | Fed. Rep. of Germany . |
| 2817576 | 11/1978 | Fed. Rep. of Germany . |

*Primary Examiner*—Edward J. Meros
*Attorney, Agent, or Firm*—Keil & Witherspoon

[57] ABSTRACT

A process for the preparation of zeolites of the ZSM-5 structural type from a mixture of $SiO_2$ and $Al(OH)_3$ by hydrothermal crystallization in an aqueous amine solution, in the absence of alkali, at from 100° to 200° C., wherein the crystallization is carried out in the presence of a triamine, tetraamine and/or higher amine and the reaction mixture is formulated to have an $SiO_2/Al_2O_3$ molar ratio defined by an equation which involves the chain length and number of amine groups of the amine employed, as well as to have certain molar ratios of $H_2O$/amine and amine/$Al_2O_3$, and the use of these zeolites as catalysts for the conversion of alcohols and/or dialkyl ethers to olefins and/or aromatics

6 Claims, No Drawings

PREPARATION OF ZEOLITES

The present invention relates to a process for the preparation of zeolites of the ZSM-5 structural type. Zeolites of the A-type, X-type, Y-type and mordenite type have become very important in industry, where they are employed as ion exchangers, molecular sieves and catalysts. Industrial processes such as catalytic cracking and hydrogenating cracking of hydrocarbons are carried out with zeolite catalysts. Recently, zeolites of the ZSM-5 type have become of increasing interest, for example for reactions such as the conversion of methanol to aromatics and/or olefins.

Zeolites are crystalline silicates, in particular aluminosilicates. To prepare aluminosilicate zeolites, reactive $SiO_2$ and $Al_2O_3$ starting materials are subjected to hydrothermal crystallization in the presence of strong bases. The strong bases employed in the conventional processes are as a rule alkali metal hydroxides or alkaline earth metal hydroxides or quaternary nitrogen bases or phosphorus bases, either individually or as mixtures with one another.

Zeolites of the ZSM-5 type were first prepared from mixtures of reactive $SiO_2$ and $Al_2O_3$ by hydrothermal crystallization in the presence of tetrapropylammonium ions and sodium ions (U.S. Pat. No. 3,702,886). A disadvantage of this method of synthesis is that it employs quaternary nitrogen bases which are difficult to obtain and that the alkali metal cations have to be replaced by other cations in order to arrive at the catalytically active form. It is known that only a particularly expensive ion exchange succeeds in removing the alkali metal ions from the cavities of ZSM-5 (German Laid-Open Application DOS 2,442,240).

Accordingly, the further development of the synthesis of zeolites of the ZSM-5 type was aimed at overcoming the above disadvantages. Processes where primary amines or diamines are used in conjunction with an alkali in place of the quaternary nitrogen bases have already been employed to prepare zeolites of the ZSM-5 type; these known processes are described in German Laid-Open Applications DOS 2,442,240, DOS 2,817,575 and DOS 2,817,576. A feature of all these processes is, however, that the synthesis still involves the presence of alkali metal ions.

It is an object of the present invention to provide a process whereby cheap starting materials can be used to synthesize novel catalytically active zeolites which are formed in an Na-free form and can therefore be employed as catalysts directly or at most after a simple calcination, but without prior ion exchange.

We have found that this object is achieved by a process for the preparation of zeolites of the ZSM-5 structural type from a mixture of $SiO_2$ and $Al(OH)_3$ by hydrothermal crystallization in an aqueous amine solution, in the absence of alkali, at from 100° to 200° C., wherein the crystallization is carried out in the presence of a triamine, tetraamine and/or higher amine and the reaction mixture is formulated to have an $SiO_2/Al_2O_3$ molar ratio which depends on the chain length $L_R$ and number of amine groups n of the amine employed and is from $$\frac{96 - \frac{20n}{L_R + 4}}{\frac{20n}{L_R + 4}} \text{ and } \frac{96 - \frac{20n}{L_R + 4}}{\frac{4n}{L_R + 4}}$$

as well as to have an $H_2O$/amine molar ratio of from 0.4 to 100 and an amine/$Al_2O_3$ molar ratio of from 5 to 400.

The process according to the invention is advantageously carried out in the presence of an organic amine which has a substantially lower basicity than an alkali or a quaternary nitrogen base, for example dipropylenetriamine, dihexamethylenetriamine, diethylenetriamine or triethylenetetramine, or in the presence of a mixture of such amines. The $SiO_2/Al_2O_3$ ratio is varied at the same time in the characteristic manner defined by the above equation.

The H-form of the zeolite can be obtained in a simple manner by removing the amine component.

The present invention also relates to the use of the zeolites prepared according to the invention, in particular in their H-form, as catalysts for the conversion of alcohols and/or dialkyl ethers to olefins and/or aromatics.

In the process according to the invention, a mixture of a reactive $SiO_2$, such as pyrogenic silica (Aerosil) and active aluminum oxide, for example freshly precipitated $Al(OH)_3$ can be crystallized under hydrothermal conditions in the presence of an organic triamine, tetraamine or more highly condensed amine, at from 100° to 200° C., especially from 140° to 170° C. The concentration of the aqueous amine solution should be advantageously from 10 to 70%, especially from 40 to 60%.

The aluminum can also be wholly or partially replaced by other trivalent elements, especially boron and/or iron. The incorporation of boron into the crystal lattice manifests itself in a shift of the d-values of the X-ray diffraction lines toward lower values.

In an advantageous embodiment of the process according to the invention, a reaction mixture of $SiO_2$ and aluminum oxide or hydroxide or of their sodium-free intermediates is prepared in the ratio stated above and is then heated in an aqueous amine solution for from 2 to 8 days at from 100° to 200° C., preferably from 1 to 4 days at from 140° to 170° C. under autogenous pressure. The zeolite thus produced as a rule contains substantial amounts of the amine employed, occluded in the intracrystalline pores. This amine can be removed from the pores by, for example, combustion, resulting in the catalytically active hydrogen form.

Advantageously, the mother liquor is entirely or partially re-used for the preparation of fresh zeolite. Table 1 below shows the maximum and minimum $SiO_2/Al_2O_3$ molar ratio calculated from the chain length of the amine used, in accordance with the equations given above, in comparison with the results of the actual crystallization experiments).

| | $L_R$ (A) | $\frac{96 - \frac{20n}{L_R + 4}}{\frac{20n}{L_R + 4}}$ | $\frac{96 - \frac{20n}{L_R + 4}}{\frac{4n}{L_R + 4}}$ | $SiO_2/Al_2O_3$ molar ratio in the crystallization experiments | Product |
|---|---|---|---|---|---|
| Triethylenetetramine | 13.4 | 19.9 | 99.4 | 15 | amorphous |
| | | | | 23 | ZSM-5 |
| | | | | 90 | ZSM-5 |

-continued

| | $L_R$ (Å) | $\dfrac{96 - \dfrac{20n}{L_R + 4}}{\dfrac{20n}{L_R + 4}}$ | $\dfrac{96 - \dfrac{20n}{L_R + 4}}{\dfrac{4n}{L_R + 4}}$ | $SiO_2/Al_2O_3$ molar ratio in the crystallization experiments | Product |
|---|---|---|---|---|---|
| Diethylenetriamine | 9.4 | 20.3 | 101.5 | 120 | ZBM-30 |
| | | | | 23 | ZSM-5 |
| | | | | 100 | ZSM-5 and ZBM-30 |
| Dihexamethylenetriamine | 20 | 37.4 | 187 | 40 | ZSM-5 |
| | | | | 160 | ZSM-5 |
| Dipropylenetriamine | 12 | 24.6 | 123 | 28 | ZSM-5 |
| | | | | 60 | ZSM-5 |
| Propylenediamine | 6.7 | 24.7 | 123.5 | 15 | Ferrierite |
| | | | | 25 | ZSM-5 |
| | | | | 70 | ZSM-5 |
| | | | | 100 | ZBM-30 and ZSM-5 |
| | | | | 150 | ZBM-30 |

EXAMPLE 1

101 g of Aerosil and freshly precipitated Al(OH)$_3$ (prepared from 49 g of Al(NO$_3$)$_3$.9H$_2$O by precipitation with ammonia) are introduced into 1,200 g of 50% strength dipropylenetriamine solution. The mixture is then stirred until it is homogeneous, after which it is heated for 7 days at 170° C. in a steel autoclave. A crystalline product is filtered off, washed and dried at 100° C. According to X-ray analysis, it consists of well-crystallized aluminum zeolite of the Pentasil type.

EXAMPLE 2

Using the method described in Example 1, 101 g of SiO$_2$ and the amount of Al(OH)$_3$ corresponding to the particular SiO$_2$/Al$_2$O$_3$ molar ratio are treated hydrothermally in 1,200 g of 50% strength amine solution for 7 days at 170° C. The amine used, the SiO$_2$/Al$_2$O$_3$ molar ratio and the character of the product obtained are shown in Table 2.

TABLE 2

| | $SiO_2/Al_2O_3$ molar ratio | Product |
|---|---|---|
| Dipropylenetriamine | 20 | amorphous |
| | 26 | ZSM-5 |
| | 60 | ZSM-5 |
| Dihexamethylenetriamine | 40 | ZSM-5 |
| | 160 | ZSM-5 |
| | 6000 | ZBM-30 |
| Triethylenetetramine | 22 | ZSM-5 |
| | 90 | ZSM-5 |
| | pure SiO$_2$ | ZBM-30 |
| Diethylenetriamine | 23 | ZSM-5 |
| | 100 | ZSM-5 and ZBM-30 |

EXAMPLE 3

100 g of Aerosil and 60 g of boric acid are introduced into 1,200 g of 50% strength triethylenetetramine solution. The mixture is then stirred until homogeneous, after which it is heated for 7 days at 170° C. in a steel autoclave. The product is filtered off, washed and dried. According to X-ray analysis, it consists of a well-crystallized boron zeolite. The SiO$_2$/B$_2$O$_3$ ratio in the product is 24.

EXAMPLE 4

100 g of the zeolite obtained with the aid of triethylenetetramine in Example 2 and having an Si/Al ratio of 22 are mixed with boehmite, and the mixture is converted to 1 mm extrudates. The zeolite content of the extrudates is 65% by weight. 20 g of the product obtained are introduced, as the catalyst, into a continuous-flow reactor, and the activity of the catalyst in converting methanol to olefins is tested. Preparation of olefins from methanol.

Methanol containing 75% by weight of water is passed over the catalyst at 330° C. The throughput is 360 g of solution/h, and 20 g of catalyst are employed. The reaction conditions are summarized below:

| Input temperature | 330° C. |
|---|---|
| Pressure | 1.16 bar |
| Conversion | 100% |

The reaction product obtained consists of 10% by weight of liquid hydrocarbons and 90% by weight of gaseous reaction products. The gaseous products in turn contain 26% by weight of C$_2$H$_4$ and 28% by weight of C$_3$H$_6$.

We claim:

1. A process for obtaining a crystalline ZSM-5 structural type zeolite of the hydrogen cation form directly which comprises reacting at from 100° to 200° C. in an aqueous solution under autogenous pressure in the absence of both alkali metal ions and quaternary nitrogen bases, and in the presence of a triamine, tetraamine and/or higher amine, an aqueous reaction mixture of SiO$_2$ and Al(OH)$_3$ formulated to have a SiO$_2$/Al$_2$O$_3$ molar ratio $$\dfrac{96 - \dfrac{20n}{L_R + 4}}{\dfrac{4n}{L_R + 4}}$$

which depends on the chain length $L_R$ and number of amine groups n of the amine employed, and an H$_2$O/amine molar ratio of from 0.4 to 100 and an amine/Al$_2$O$_3$ molar ratio of from 5 to 400, and removing the amine from the zeolite pores by combustion.

2. The process for obtaining a crystalline zeolite as recited in claim 1, wherein the aqueous solution has a concentration of triamine, tetraamine and/or higher amine of 10 to 70% by weight.

3. The process for obtaining a crystalline zeolite as recited in claim 1, wherein reaction takes place at from 140° to 170° C.

4. The process for obtaining a crystalline zeolite as recited in claim 1, wherein the aqueous solution has a concentration of triamine, tetraamine and/or higher amine of 40 to 60% by weight.

5. The process for obtaining a crystalline zeolite as recited in claim 1, wherein reaction takes place for from 2 to 8 days.

6. The process for obtaining a crystalline zeolite as recited in claim 3, wherein reaction takes place for from 1 to 4 days.

* * * * *